(12) United States Patent
Zar

(10) Patent No.: US 6,560,780 B2
(45) Date of Patent: May 13, 2003

(54) HEADWARE

(76) Inventor: Clive Elchonon Zar, 1 P O Box 27832, Yeoville (ZA), 2143

( * ) Notice: Subject to any disclaimer, the term of this patent is extended or adjusted under 35 U.S.C. 154(b) by 0 days.

(21) Appl. No.: 09/844,454

(22) Filed: Apr. 27, 2001

(65) Prior Publication Data

US 2001/0037517 A1 Nov. 8, 2001

(30) Foreign Application Priority Data

Apr. 28, 2000 (ZA) .............................. 00/2138

(51) Int. Cl.$^7$ ................................ A61F 9/00
(52) U.S. Cl. ............................................. 2/12
(58) Field of Search .................... 2/12, 10, 455, 2/175.1, 195.1, 171.1, 183

(56) References Cited

U.S. PATENT DOCUMENTS

| 729,500 | A | * | 5/1903 | Mahony | 2/12 |
| 2,160,513 | A | * | 5/1939 | Pastermak | 2/12 |
| 4,920,576 | A | * | 5/1990 | Landis | 2/9 |
| 4,945,575 | A | * | 7/1997 | Townsend | 2/9 |
| 5,647,060 | A | * | 7/1997 | Lee | 2/9 |
| 5,857,218 | A | * | 1/1999 | Kuhlmann et al. | 2/174 |
| 6,009,555 | A | * | 1/2000 | Siprut | 2/12 |
| 6,216,282 | B1 | * | 4/2001 | Marzec | 2/452 |

* cited by examiner

Primary Examiner—John J. Calvert
Assistant Examiner—Katherine Moran
(74) Attorney, Agent, or Firm—Akerman Senterfitt

(57) ABSTRACT

A peak including a peak part and an elongated substantially rectangular retaining band both die cut from closed cell foamed plastic material. A pair of openings are formed respectively at the corners of the peak part. A pair of apertures are provided at each end of the retaining band. Dumbbell shaped connectors connect the band to the peak part. Each connector passes through one of each pair of apertures and a registering opening. By having two apertures at each end of the band, the length of the band can be adjusted.

17 Claims, 3 Drawing Sheets

HEADWARE

BACKGROUND OF THE INVENTION

1. Field of the Invention

This invention relates to headware and in particular to peaks.

2. Description of the Prior Art

Peaks are widely used by runners and others who exercise in the open to protect their eyes from direct sunlight. Peaks comprise a peak part terminating at pointed ends and a retaining band that is use passes around the back of the head of the user. The retaining band may be a simple elastic string or elastic strip secured at its ends to the peak. These elastic strings and strips have in use proved ineffective because either (a) they are uncomfortably tight or (b) they tend to stretch and within a short period of time are unable to hold the peak firmly in position. Fixed bands of relatively inelastic material have been used as retaining bands but these have the disadvantage that the circumference of runners heads tend to vary so that large numbers of size of peaks have to be provided.

A separate retaining band has been provided with press button parts with corresponding parts on the peak so that the length of the band can be adjusted as desired. This arrangement has proved to be successful. However each complete push button pair comprises four parts. They are costly and the mounting is labour intensive. Consequently the peak is relatively expensive.

SUMMARY OF THE INVENTION

According to one aspect of the present invention there is provided a peak comprising a peak part having an opening at each end, a separate retaining band having a plurality of apertures at each end and separate connectors each passing through an opening and an aligned aperture to hold the retaining band to the peak. There may be two openings at each end of the peak.

The connectors may preferably each comprise a connector shank having enlarged end pieces extending transversely to the shank. These end pieces may be circular in plan. Alternatively they may be oval or any other convenient shape. The connectors are preferably soft plastics or rubber members.

The peak portion and the retaining band are preferably die cut from foam material.

BRIEF DESCRIPTION OF THE DRAWINGS

An embodiment of the invention will now be described by way of example with reference to the accompanying drawings.

In the drawings.

DESCRIPTION OF THE PREFERRED EMBODIMENT

Figure 2:
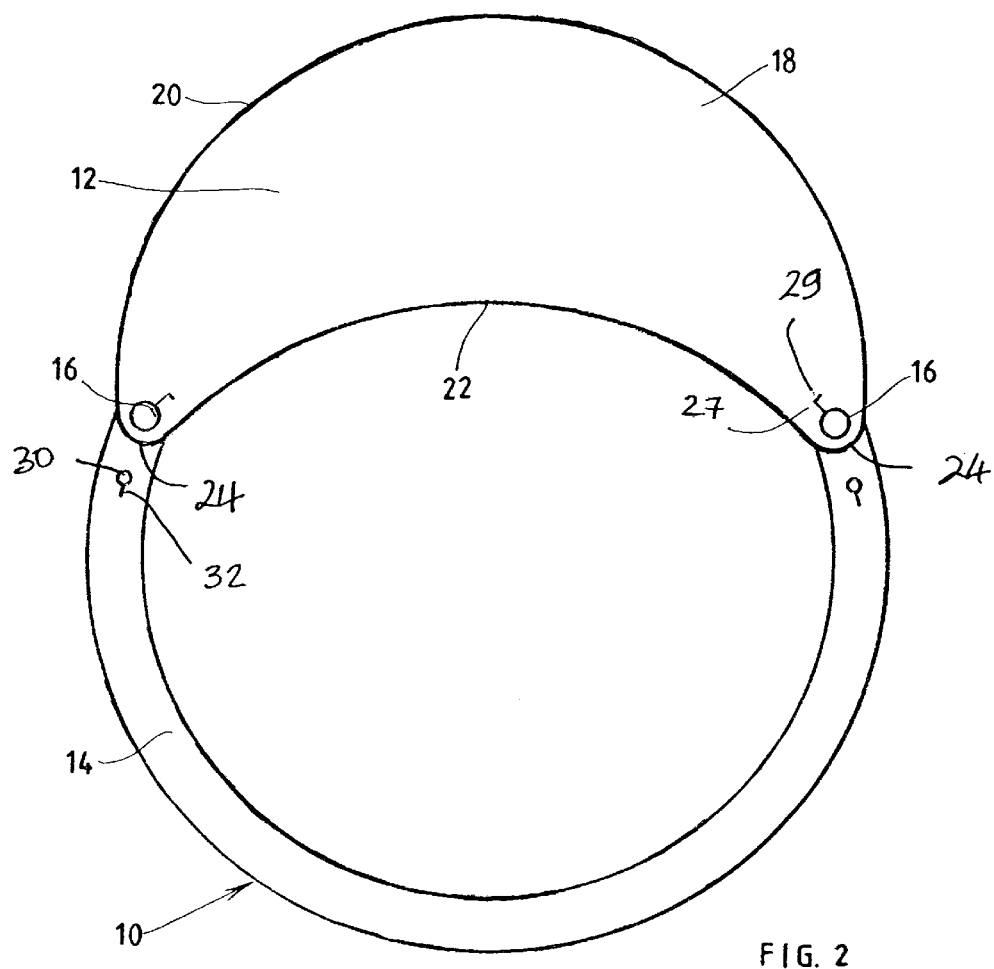
FIG. 2 is a plan of the peak.
Figure 1:
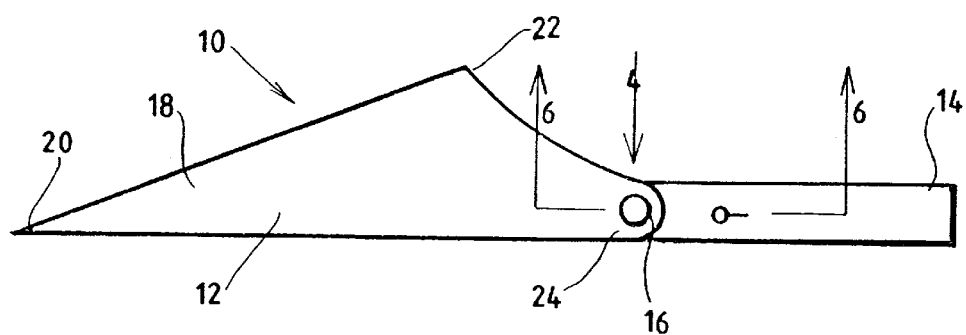
FIG. 1 is a side view of a peak of the invention.
Figure 3:
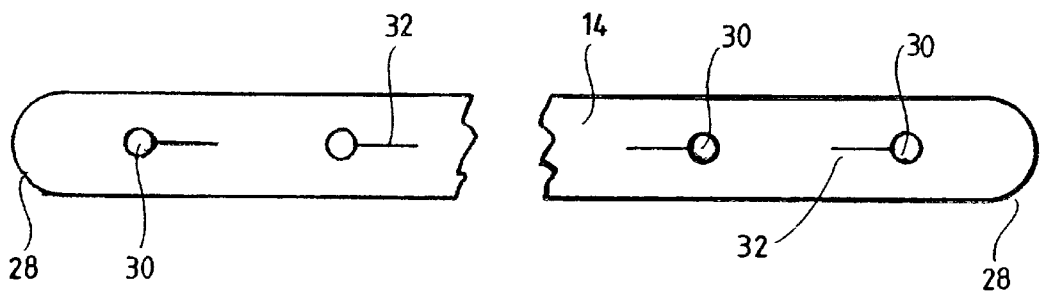
FIG. 3 is a detail broken view of the retaining band illustrating the ends of the band.

Referring now to FIGS. 1 and 2 there is shown a peak 10 comprising a peak portion 12 and a retaining band 14 joined thereto by connectors 16. The portion 12 and band 14 are die cut from closed cell foam ethyl vinyl acetate sheet having a thickness of about 3,5 mm to 4,5 mm. The material has a density of 0,161 g/cm$^3$ and 15° to 18° Shore hardness. The peak portion 12 has a front part 18 of generally segment shape, i.e. having a convex front edge 20 and concave rear edge 22 of smaller radius, and terminating in two pointed ends 24. A circular opening 26 is provided close to each end 24. A cut 27 is provided diametrically through each opening 26 to one side only, being away from the nearer end 28 and running parallel to the axis of the band 14. There is a small further cut or nib 29 at the free end of the cut at right angles thereto.

The retaining band 14 is of generally elongated rectangular shape with rounded ends 28. Two apertures 30 are provided adjacent each end 28. Each aperture 30 is circular. A cut 32 is provided radially through each aperture to one side only, being away from the nearer end 28 and running parallel to the axis of the band 14.

Each connector 16 comprises a connector shank 34 having an enlarged end piece or head 36 at each end. Each end piece 36 is generally disc like (i.e. circular in plan) extending transversely to the shank 34 and having a diameter of about twice that of the shank. The connectors 16 comprise ABS or polypropylene mouldings.

The apertures 30 are twice the diameter of the shank 34 and the overall length of each cut 32 is about five times this dimension of the shank 34.

Figure 4:
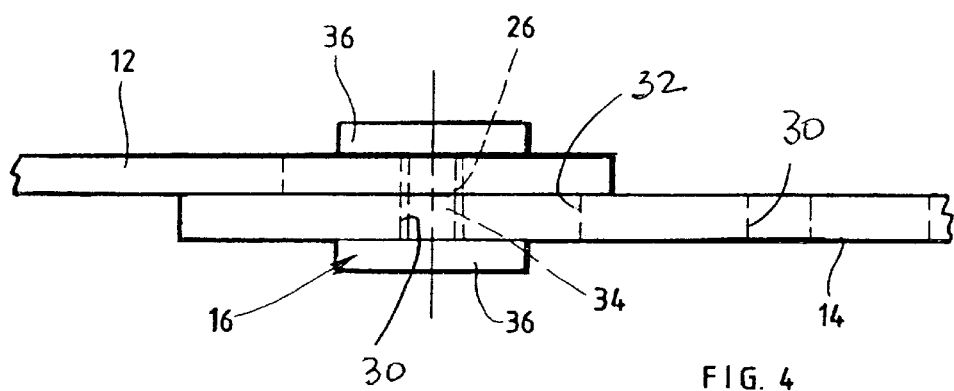
FIG. 4 is an enlarged detail plan in the direction of arrow 4 of FIG. 1.
Figure 5:
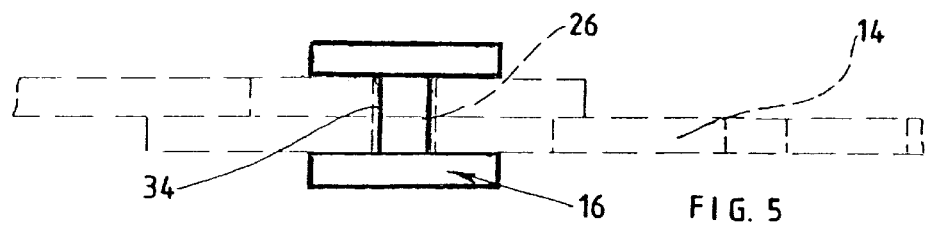
FIG. 5 is a side view of a connector.
Figure 6:
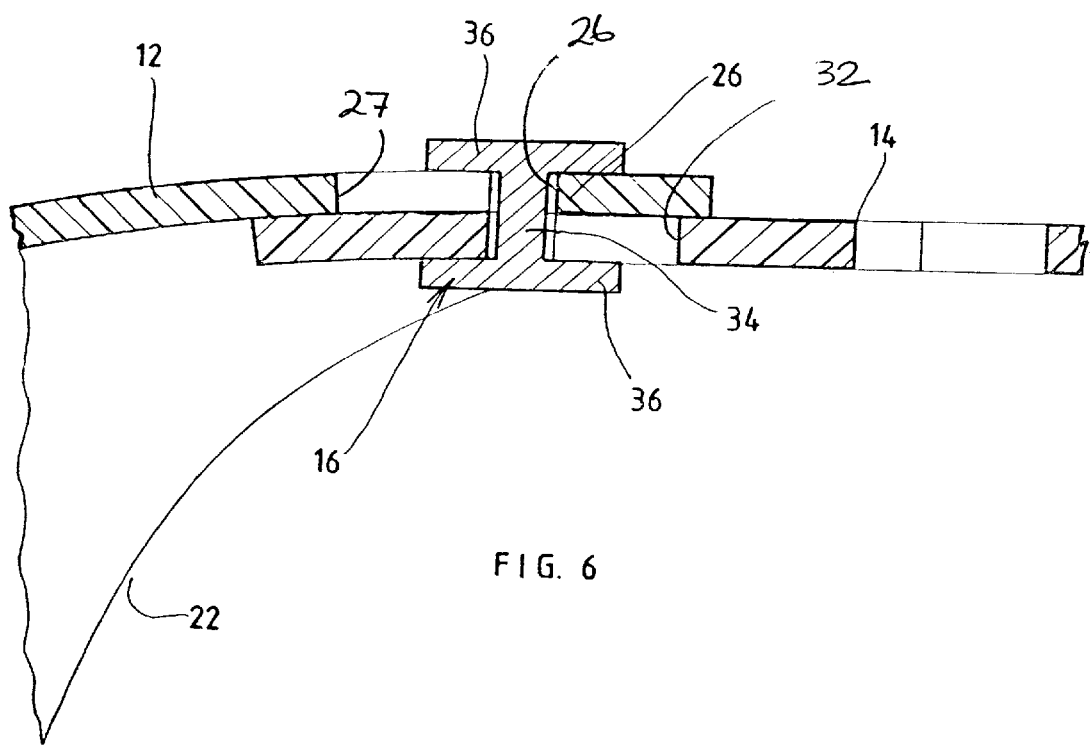
FIG. 6 is a cross-sectional view in the direction of arrow 6 of FIG. 1.

Typical dimensions are as follows: Shank diameter is 2 mm; end piece diameter is 9.5 mm; the distance between end pieces (or length of shank) is 8.5 mm; the diameter of apertures 5 mm, diameter of openings 26 is 2.3 mm, the length of retaining band 14 is 404 mm and the distance apart of outermost apertures 30 is 370 mm; the length of cuts 27 and 32 is 9 mm; and the length of nib 29 is 22 mm The connectors 16 are passed through the openings 26. The peak 10 is supplied with the peak portion 12 and retaining band 14 fiat. When a person wishes to use the peak, the connectors are passed respectively through a selected two apertures respectively at the ends of the band 14. These two apertures are now aligned respectively with the openings 26 as shown in FIGS. 4, 5 and 6. The peak 10 then takes up the position illustrated in FIG. 1.

We have found that the peak can be adjusted for a fair number of sizes of human head. The retaining band holds the peak firmly on the head for a reasonable length of time i.e. for the length of time for running a marathon or longer race. The adjustment of the size of the retaining band is easy and quick to effect. Because the end parts are flat, they will merge into the material of the retaining band and will not be raised such as to irritate the head of the user. Being formed of closed cell foam neither the retaining band or the peak will normally absorb perspiration and become damp in use.

The invention is not limited to the precise constructional details hereinbefore described and illustrated in the drawings. For example there may be more than one opening at each end of the peak portion. There may be more than two apertures at each end of the retaining band. The end parts of the connectors may be oval or any other convenient shape instead of circular. One or more of the end parts may also be rather thicker than shown so that the connector would be dumbbell shape or alternatively have one end, which is normally on the inside, substantially flat and the other of substantially spherical shape. The connectors may comprise soft plastics or rubber members. The various dimensions and materials mentioned may be varied as desired.

What is claimed is:

1. A peak comprising:
    a peak part having an opening at each end;
    a separate elongated retaining band with two ends having a plurality of apertures at each end, a cut being provided extending radially of each aperture; and
    separate connectors each passing through an opening and an aligned aperture to hold the retaining band to the peak;
    wherein said cut extends to one side only of each aperture in a direction away from the nearer end of the band.

2. A peak as claimed in claim 1, wherein each connector comprises a connector shank having enlarged end pieces extending transversely to the shank.

3. A peak as claimed in claim 2 wherein the said end pieces are circular in plan.

4. A peak as claimed in claim 2 wherein the end pieces are substantially flat.

5. A peak as claimed in claim 1, wherein a cut is provided for each opening extending radially thereof.

6. A peak as claimed in claim 1, wherein the peak portion is die cut from the sheet foam material.

7. A peak as claimed in 1, wherein the retaining band is die cut from sheet foam material.

8. A peak as claimed in claim 1, wherein the ends of the retaining band respectively overlap the ends of the peak part.

9. A peak comprising:
    a peak part having an opening at each end;
    a cut extending radially from the openings in each end of the peak part;
    a separate elongated retaining band with two ends having a plurality of apertures at each end; and
    separate connectors each passing through an opening and an aligned aperture to hold the retaining band to the peek, wherein said cut extends to one side only of each opening.

10. A peak as claimed in claim 9 wherein the cut extends in a direction away from the nearer end of the band.

11. A peak as claimed in claim 9 wherein the cut terminates in a short cut at an angle thereto.

12. A peak as claimed in claim 9, wherein each connector comprises a connector shank having enlarged end pieces extending transversely to the shank.

13. A peak as claimed in claim 9 wherein the peak portion is die cut from sheet foam material.

14. A peak as claimed in claim 9, wherein the retaining band is die cut from sheet foam material.

15. A peak as claimed in claim 9, wherein the ends of the retaining band respectively overlap the ends of the peak part.

16. A peak comprising:
    a part die cut from foam sheet material and being of generally segment shape having
        an arcuate concave inner edge and an arcuate convex outer edge,
        two pointed ends at which the said edges meet,
        a circular opening at each end, and
        an extension cut extending radially of each opening in a direction away from the adjacent pointed end;
    a separate elongated retaining band cut from foam sheet material having
        two ends,
        a plurality of circular apertures at each end, and
        an extension cut extending radially of each aperture in a direction away from the adjacent end; and separate connectors, each passing through an opening and an aligned aperture to hold the retaining band to the peak, each said connector having
        a connector shank, and
        enlarged substantially flat end pieces extending transversely to the shank.

17. A peak as claimed in claim 16 wherein the cut through each opening terminates in a short cut at an angle thereto.

* * * * *